(12) United States Patent
Brown et al.

(10) Patent No.: US 10,653,430 B2
(45) Date of Patent: May 19, 2020

(54) ARTERIAL COMPRESSION DEVICE AND METHODS OF USING THE SAME

(71) Applicant: Vascular Perspectives Limited, Manchester (GB)

(72) Inventors: Adrian D. Brown, West Yorkshire (GB); Jonathan C. Swift, Hertfordshire (GB); Christopher Brown, Cheshire (GB)

(73) Assignee: CORMED LIMITED, Cheadle (GB)

( * ) Notice: Subject to any disclaimer, the term of this patent is extended or adjusted under 35 U.S.C. 154(b) by 296 days.

(21) Appl. No.: 15/718,580

(22) Filed: Sep. 28, 2017

(65) Prior Publication Data

US 2019/0090886 A1    Mar. 28, 2019

(51) Int. Cl.
*A61B 17/135* (2006.01)
*A61B 17/132* (2006.01)

(52) U.S. Cl.
CPC .......... *A61B 17/135* (2013.01); *A61B 17/132* (2013.01); *A61B 17/1322* (2013.01); *A61B 17/1325* (2013.01)

(58) Field of Classification Search
CPC .............. A61B 17/132; A61B 17/1322; A61B 17/1325; A61B 17/1327; A61B 17/135
See application file for complete search history.

(56) References Cited

U.S. PATENT DOCUMENTS

| | | | |
|---|---|---|---|
| 2010/0280541 A1* | 11/2010 | Lampropoulos ... | A61B 17/1325 606/203 |
| 2011/0202089 A1* | 8/2011 | Sun .................... | A61B 17/1325 606/201 |
| 2014/0142615 A1* | 5/2014 | Corrigan, Jr. ...... | A61B 17/1325 606/201 |

* cited by examiner

*Primary Examiner* — Melanie R Tyson
(74) *Attorney, Agent, or Firm* — Taft Stettinus & Hollister LLP; Stephen F. Rost

(57) ABSTRACT

An arterial compression device having a band for securably fastening the arterial compression device around a wrist of a subject, a compression portion that is moveable so as to selectively apply pressure to the radial artery of the subject, and an aperture permitting access to the ulnar artery of the subject when the arterial compression device is securably fastened around the wrist of the subject.

15 Claims, 4 Drawing Sheets

ARTERIAL COMPRESSION DEVICE AND METHODS OF USING THE SAME

The present disclosure relates to an arterial compression device, and in particular to an arterial compression device for applying pressure to the radial artery of a subject. The present disclosure also relates to methods of using an arterial compression device.

BACKGROUND

Increasingly, the radial artery is used for access to the arterial vasculature when performing interventional procedures such as angiography or percutaneous coronary intervention (PCI) procedures. This is in contrast to alternative access sites, such as the femoral artery. Radial artery access may be considered to be preferable over femoral artery access for certain procedures as it may allow vascular closure in a vessel that is more easily closed. This may result in less hospital-based recovery time for the patient thereby reducing costs and improving patient comfort.

Following a transradial catheterization procedure, closure of the radial artery puncture site can occasionally result in permanent occlusion of the radial artery. In the event that the adjacent ulnar artery is not fully functional, occlusion of the radial artery may lead to improper perfusion of the hand. Furthermore, loss of radial artery patency (normal blood flow) can prohibit future use of the radial artery for further procedures.

It is known to provide an arterial compression device to provide a compressive force to the radial artery following transradial catheterization with the aim of achieving patent hemostasis. Known arterial compression devices include bands that are secured around the wrist of the patient, where the devices additionally include a movable pad or inflatable bladder for applying the compressive force to the radial artery. Such arterial compression devices may be used for several hours following removal of a sheath/cannula from the radial artery puncture site to achieve patent hemostasis.

There exists a need, however, for providing an improved arterial compression device and methods of using the same.

It is an object of embodiments of the present disclosure to provide an arterial compression device and methods of using an arterial compression device that overcome certain disadvantages associated with the prior art.

BRIEF SUMMARY OF THE DISCLOSURE

In accordance with a first aspect of the present disclosure there is provided an arterial compression device including a band for securably fastening the arterial compression device around a wrist of a subject; a compression portion that is moveable so as to selectively apply pressure to the radial artery of the subject; and an aperture permitting access to the ulnar artery of the subject when the arterial compression device is securably fastened around the wrist of the subject.

The presence of the aperture advantageously permits selective temporary compression (and therefore occlusion) of the ulnar artery whilst the compression portion is applied against the radial artery of the subject. The arterial compression device according to embodiments of the present disclosure may therefore permit improved assessment of radial artery patency. This is in contrast with prior art arterial compression devices whereby the devices obstruct access to the ulnar artery and thereby make assessment of radial artery patency difficult whilst the devices are fastened around the wrist of a subject. The present disclosure may therefore facilitate better assessment of radial artery patency to improve the likelihood of achieving patent hemostasis, and therefore reduce the occurrence of radial artery occlusion following transradial catheterization.

In certain embodiments, the compression portion may include a pad for contacting the wrist of the subject to apply pressure to the radial artery of the subject. In certain embodiments, the pad may comprise silicone. In certain embodiments, the pad may have a flat surface for contacting the wrist of the subject. In certain embodiments, the pad may have a length of between 40 mm and 50 mm, and preferably may have a length of 44 mm. In certain embodiments, the pad may have a width of between 20 mm and 30 mm, and preferably may have a width of 26 mm.

The arterial compression device may further comprise a rotatable knob that is rotatably coupled to the pad such that rotation of the knob about an axis causes movement of the pad along the axis.

Additionally or alternatively, the pad may include a first groove for accommodating a cannula inserted into a puncture site of the subject beneath the pad when the pad is in contact with the wrist of the subject. In certain embodiments, the pad may include a second groove opposing the first groove wherein the first groove may accommodate a cannula when the device is positioned on a subject's left wrist and the second groove may accommodate a cannula when the device is positioned on a subject's right wrist.

In alternative embodiments, the compression portion may comprise an inflatable balloon for applying pressure to the radial artery of the subject.

The arterial compression device may further comprise a wrist plate having a first end and a second end, wherein the band is connected to the wrist plate at the first end and the second end. In such embodiments, the aperture may be at least partly formed through the wrist plate. The aperture may have a generally quadrilateral shape that is bound on at least three sides by the wrist plate. In alternative embodiments, the aperture may have a generally quadrilateral shape that is bound on four sides by the wrist plate.

In certain embodiments, the wrist plate may be transparent or translucent. Additionally or alternatively, the compression portion may be transparent or translucent. Additionally or alternatively, the rotatable knob may be transparent or translucent. The use of transparent or translucent components may facilitate visual inspection of the puncture site (e.g. to check for bleeding).

The aperture is sized so as to permit access to the ulnar artery of the subject when the arterial compression device is securably fastened around the wrist of the subject. In certain embodiments, the aperture may have a width of at least 2 cm and/or has a length of at least 2 cm. In certain embodiments, the aperture may encompass an area of at least 2×2 cm$^2$.

In accordance with a second aspect of the present disclosure there is provided a method of assessing radial artery patency in a subject including:
  (i) providing an arterial compression device comprising:
    a band for securably fastening the arterial compression device around a wrist of the subject;
    a compression portion that is moveable so as to selectively apply pressure to the radial artery of the subject; and
    an aperture permitting access to the ulnar artery of the subject when the arterial compression device is securably fastened around the wrist of the subject;
  (ii) securably fastening the arterial compression device around the wrist of the subject;

(iii) moving the compression portion to apply pressure to the radial artery of the subject;
(iv) manually occluding the ulnar artery of the wrist by applying pressure to the ulnar artery through the aperture;
(v) making a first determination of a pulse of the subject in a finger of a hand connected to the wrist;
(vi) moving the compression portion to reduce the pressure applied to the radial artery;
(vii) making a second determination of the pulse of the subject in the finger of the hand connected to the wrist;
(viii) comparing the first determination with the second determination; and
(ix) determining whether radial artery patency has been achieved based on the comparison.

In certain embodiments, the step of making a first determination and/or making a second determination may comprise using a pulse oximeter to measure the pulse of the subject.

In certain embodiments, the compression portion may include a pad for contacting the wrist of the subject to apply pressure to the radial artery of the subject. In certain embodiments, the pad may comprise silicone. In certain embodiments, the pad may have a flat surface for contacting the wrist of the subject. In certain embodiments, the pad may have a length of between 40 mm and 50 mm, and preferably may have a length of 44 mm. In certain embodiments, the pad may have a width of between 20 mm and 30 mm, and preferably may have a width of 26 mm.

The arterial compression device may further comprise a rotatable knob that is rotatably coupled to the pad such that rotation of the knob about an axis causes movement of the pad about the axis.

Additionally or alternatively, the pad may include a first groove for accommodating a cannula inserted into a puncture site of the subject beneath the pad when the pad is in contact with the wrist of the subject. In certain embodiments, the pad may include a second groove opposing the first groove wherein the first groove may accommodate a cannula when the device is positioned on a subject's left wrist and the second groove may accommodate a cannula when the device is positioned on a subject's right wrist.

In alternative embodiments, the compression portion may comprise an inflatable balloon for applying pressure to the radial artery of the subject.

The arterial compression device may further comprise a wrist plate having a first end and a second end, wherein the band is connected to the wrist plate at the first end and the second end. In such embodiments, the aperture may be at least partly formed through the wrist plate. The aperture may have a generally quadrilateral shape that is bound on at least three sides by the wrist plate. In alternative embodiments, the aperture may have a generally quadrilateral shape that is bound on four sides by the wrist plate.

In certain embodiments, the wrist plate may be transparent or translucent. Additionally or alternatively, the compression portion may be transparent or translucent. Additionally or alternatively, the rotatable knob may be transparent or translucent. The use of transparent or translucent components may facilitate visual inspection of the puncture site (e.g. to check for bleeding).

The aperture is sized so as to permit access to the ulnar artery of the subject when the arterial compression device is securably fastened around the wrist of the subject. In certain embodiments, the aperture may have a width of at least 2 cm and/or has a length of at least 2 cm. In certain embodiments, the aperture may encompass an area of at least 2×2 $cm^2$.

In accordance with a third aspect of the present disclosure there is provided an arterial compression device comprising:
a band for securably fastening the arterial compression device around a wrist of a subject; and
a compression portion that is moveable so as to selectively apply pressure to the radial artery of the subject;
wherein the compression portion includes a pad for contacting the wrist of the subject to apply pressure to the radial artery of the subject; and
the pad includes a first groove for accommodating a cannula inserted into a puncture site of the subject beneath the pad when the pad is in contact with the wrist of the subject.

The groove may advantageously assist the aligned removal of a cannula from beneath the compression portion when the compression portion is in contact with the wrist of the subject. In certain embodiments, the pad may include a second groove opposing the first groove wherein the first groove may accommodate a cannula when the device is positioned on a subject's left wrist and the second groove may accommodate a cannula when the device is positioned on a subject's right wrist.

In certain embodiments, the pad may have a flat surface for contacting the wrist of the subject. In certain embodiments, the pad may have a length of between 40 mm and 50 mm, and preferably may have a length of 44 mm. In certain embodiments, the pad may have a width of between 20 mm and 30 mm, and preferably may have a width of 26 mm. In certain embodiments, the pad may comprise silicone.

The arterial compression device may further comprise a rotatable knob that is rotatably coupled to the pad such that rotation of the knob about an axis causes movement of the pad along the axis.

The arterial compression device may further comprise a wrist plate having a first end and a second end, wherein the band is connected to the wrist plate at the first end and the second end. In such embodiments, the aperture may be at least partly formed through the wrist plate. The aperture may have a generally quadrilateral shape that is bound on at least three sides by the wrist plate. In alternative embodiments, the aperture may have a generally quadrilateral shape that is bound on four sides by the wrist plate.

In certain embodiments, the wrist plate may be transparent or translucent. Additionally or alternatively, the compression portion may be transparent or translucent. Additionally or alternatively, the rotatable knob may be transparent or translucent. The use of transparent or translucent components may facilitate visual inspection of the puncture site (e.g. to check for bleeding).

In certain embodiments, the arterial compression device may include an aperture for permitting access to the ulnar artery of the subject when the arterial compression device is securably fastened around the wrist of the subject. The aperture may be sized so as to permit access to the ulnar artery of the subject when the arterial compression device is securably fastened around the wrist of the subject. In certain embodiments, the aperture may have a width of at least 2 cm and/or has a length of at least 2 cm. In certain embodiments, the aperture may encompass an area of at least 2×2 $cm^2$.

BRIEF DESCRIPTION OF THE DRAWINGS

Embodiments of the disclosure are further described hereinafter with reference to the accompanying drawings, in which.

DETAILED DESCRIPTION

Figure 1:
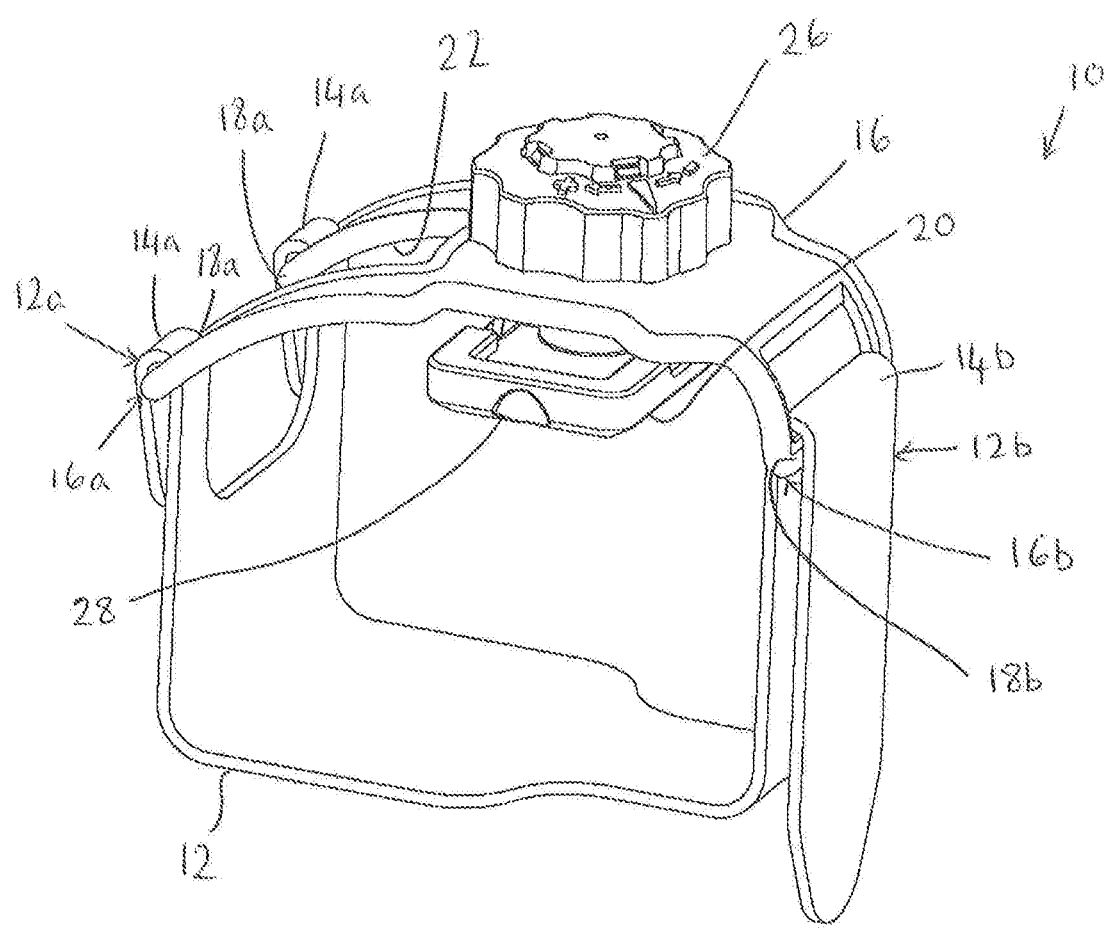
FIG. 1 is a perspective view of an arterial compression device according to an embodiment of the present disclosure.

An arterial compression device 10 according to an embodiment of the present disclosure is shown in FIG. 1. The arterial compression device 10 includes a band 12 for securably fastening the device 10 around a wrist of a subject, and a compression portion in the form of a pad 20. The pad 20 is located on the device 10 in a position such that it is moveable so as to selectively apply pressure to the radial artery of the subject when the device 10 is secured around the wrist of the subject. The pad may be made of or include silicone or a similarly soft and/or resilient material. In certain embodiments, the pad 20 may include a rigid back plate and a soft contact portion for contacting the subject.

In the non-limiting embodiment shown in FIG. 1, the device 10 includes a wrist plate 16 to which the pad 20 is connected. The wrist plate 16 has a first end 16a that is connected to a first end 12a of the band 12. In the non-limiting embodiment shown in the Figures, the wrist plate 16 has a pair of first bars 18a at the first end 16a of the wrist plate 16, and the wrist plate 16 further has a second bar 18b at the second end 16b of the wrist plate 16. In the illustrated embodiment, the first end 12a of the band 12 is formed into a pair of first loops 14a that each pass over one of the first bars 18a. Similarly, the second end 12b of the band 12 is formed into a loop 14b that passes over the second bar 18b. The first loops 14a and second loop 14b may be formed by any suitable attachment of the band 12 to itself to form such loops. For example, hook and eye fasteners (e.g. Velcro®), adhesive, stud fasteners or a buckle may provide an attachment of the band 12 to itself to form the first loops 14a and/or the second loop 14b. Any or all of the first loops 14a and the second loop 14b may be releasably openable so as to permit adjustment of the length of the band 12 to facilitate locating and securing of the device 10 on the wrist of a subject.

Figure 4:
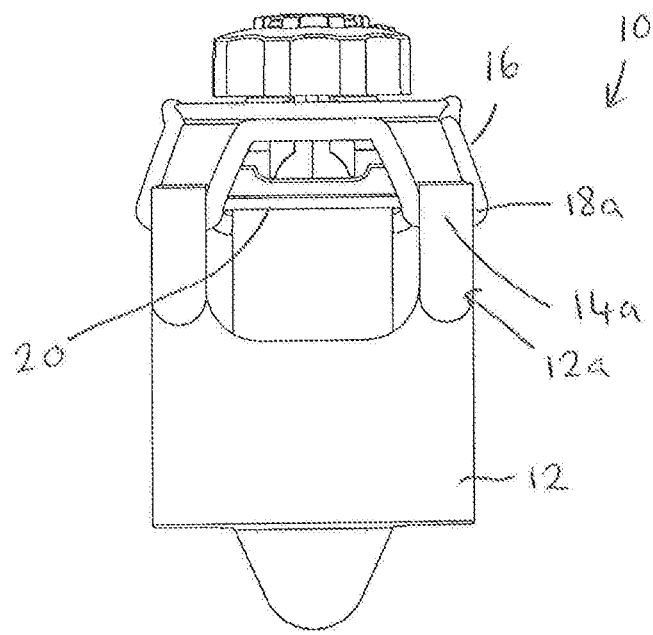
FIG. 4 is a rear end view of the arterial compression device of FIG. 1.
Figure 5:
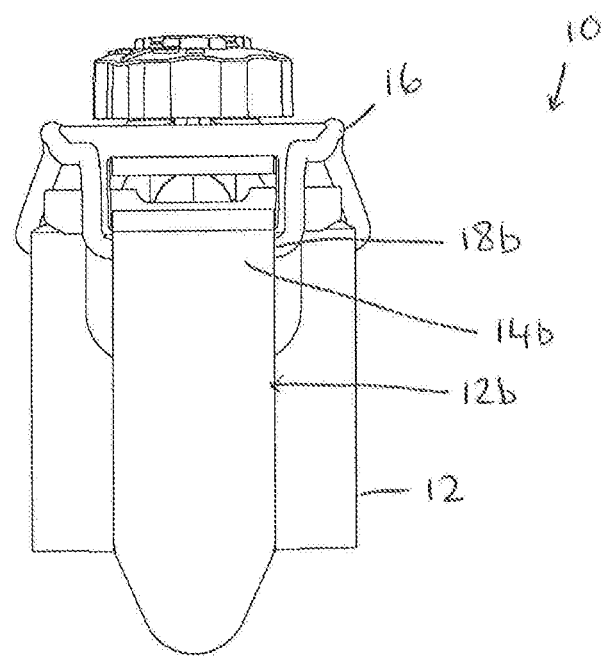
FIG. 5 is a front end view of the arterial compression device of FIG. 1.

FIGS. 4 and 5 show end views of the device 10 in which the connection between the band 12 and the wrist plate 16 can be seen in further detail.

In certain embodiments, any number of first loops 14a and second loops 14b may be provided at the first and second ends 12a, 12b of the band 12. The first and second bars 18a, 18b for receiving the first and second loops 14a, 14b may each be defined by apertures in the wrist plate 16 (as illustrated). In alternative embodiments, the first bar(s) 18a and/or second bar 18b (or multiple second bars) may comprise a protrusion extending from the wrist plate 16 for receiving the first loop(s) 14a and second loop(s) 14b. In alternative embodiments, the first/second bars 18a, 18b and/or first/second loops 14a, 14b may not be present and alternative connections mean may be provided between the band 12 and the wrist plate 16.

Figure 2A:
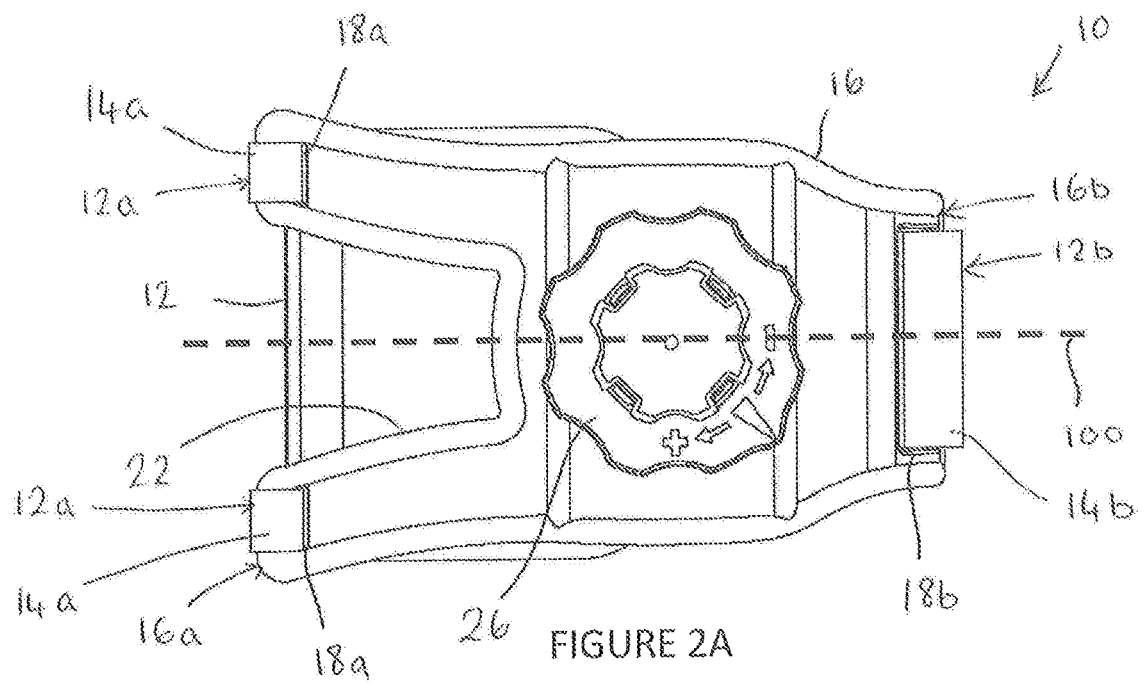
FIG. 2A is a top view of the arterial compression device of FIG. 1.

FIG. 2A shows a top view of the device 10 of FIG. 1. As shown in FIG. 2A, the device 10 extends generally in a circumferential direction along a plane 100 to form a closed (or at least closable) loop that may be placed around the wrist of a subject.

The device 10 includes an aperture 22 that permits access to the ulnar artery of the subject when the arterial compression device is securably fastened around the wrist of the subject. That is, a thumb, one or more fingers, or other instruments for applying a pressure to the ulnar artery may access a site on the wrist of the subject wearing the device 10 in order to manually occlude the ulnar artery. In the non-limiting embodiment shown in the Figures, the aperture 22 of the device 10 is formed through both the wrist plate 16 and the band 12. That is, the aperture 22 is partly bound by edges of the wrist plate 16 and partly bound by edges of the band 12. In particular, the aperture 22 is generally a quadrilateral shape that is bound on one side by an edge of the wrist plate 16, on an opposite side by an edge of the band 12, and on the two additional sides partly by the wrist plate 16 and partly by the band 12.

Figure 2B:
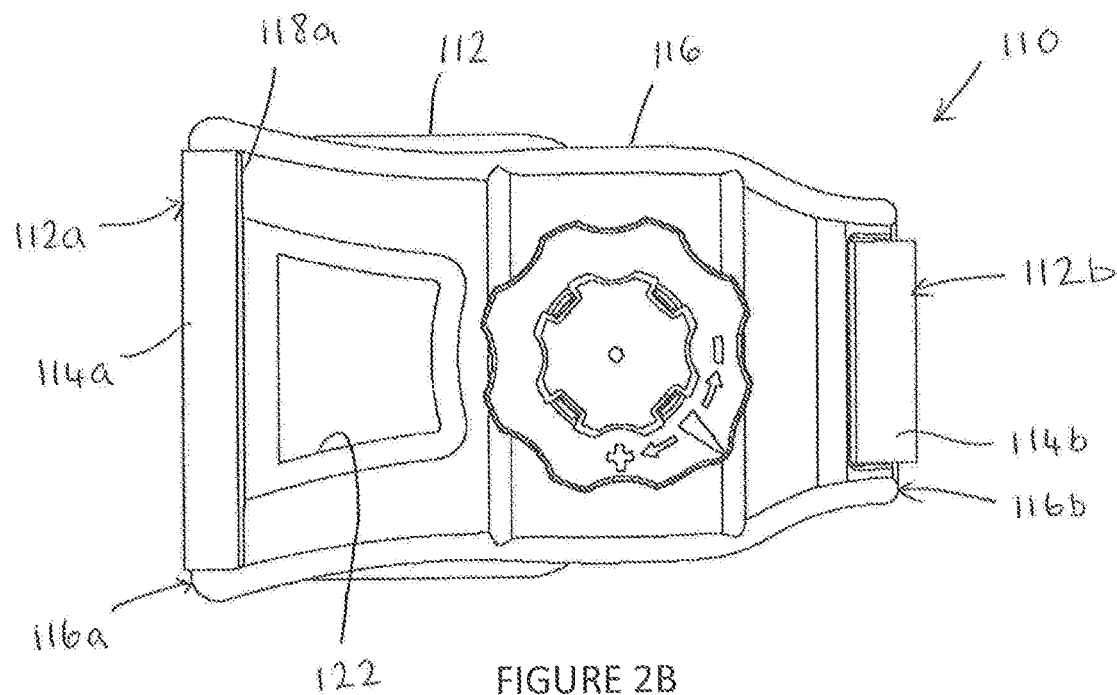
FIG. 2B is a top view of an arterial compression device according to an alternative embodiment of the present disclosure.

In alternative embodiments, the aperture 22 may be otherwise defined. For example, in an alternative embodiment that is depicted in FIG. 2B, the aperture 122 of the device 110 is defined solely by edges of the wrist plate 116 (in the embodiment depicted in FIG. 2B, features of the device 110 that correspond to features of the device 10 are numbered using the same reference numerals but with a leading '1'). The aperture may be generally quadrilateral or otherwise shaped (e.g. polygonal, circular or an irregular shape). Edges of the wrist plate 16 and/or band may bound the aperture 22 either partly or entirely.

In certain embodiments, the aperture 22 is sized to permit at least one thumb tip to pass therethrough so as to apply a pressure to the wrist that may temporarily occlude the ulnar artery. In certain embodiments, the aperture 22 has a width that is 2 cm or greater and/or a length that is 2 cm or greater. In certain embodiments, the aperture 22 includes an area that is 4 cm$^2$ or greater.

The aperture 22 is located on the device 10 adjacent to the pad 20 and at a distance from the pad 20 (along the circumferential direction in plane 100) such that, when the device 10 is secured to the wrist of a subject, the pad 20 may selectively apply pressure to the radial artery of the subject whilst the aperture 22 is positioned on the device 10 relative to the pad 20 such that the ulnar artery may be accessed. The position of the pad 20 may be adjusted to apply, increase, and/or decrease pressure applied to the radial artery. Furthermore, the position of the pad 20 may be adjusted so as to remove any pressure applied to the radial artery.

In practice, the angle at which the patient's skin is punctured to insert the sheath/cannula is likely to vary between different medical professionals and their respective preferences. If the angle is more acute, then there will likely be a greater longitudinal distance (perpendicular to plane 100) between the puncture site of the skin (which is visible) and the puncture site of the radial artery (which may not be visible). In an example of a very acute angle of puncture (e.g. less than 10 degrees relative to the patient's skin), positioning the device 10 on a patient's wrist above the puncture site of the skin may not necessarily position the device 10 directly above the puncture site of the radial artery. In such a position, there is a risk that compressing a prior art device may undesirably not apply compression at the puncture site of the radial artery to achieve hemostasis. As such, the pad 20 of the present disclosure has a flat surface to contact the patient's skin. Having a flat surface may advantageously increase the surface area through which compression can be applied, which may advantageously reduce the risks associated with applying the device 10 to a patient's wrist that has a more acute angle of puncture.

The pad 20 may have a length (perpendicular to plane 200) of between 40 mm and 50 mm, preferably 44 mm. The pad 20 may have a width (parallel to plane 200) of between 20 mm and 30 mm, preferably 26 mm. Such dimensions may advantageously provide for a surface area suitable for reducing the risks associated with applying the device 10 to a patient's wrist at an acute angle to the skin (e.g. 10 degrees or less).

Figure 3A:
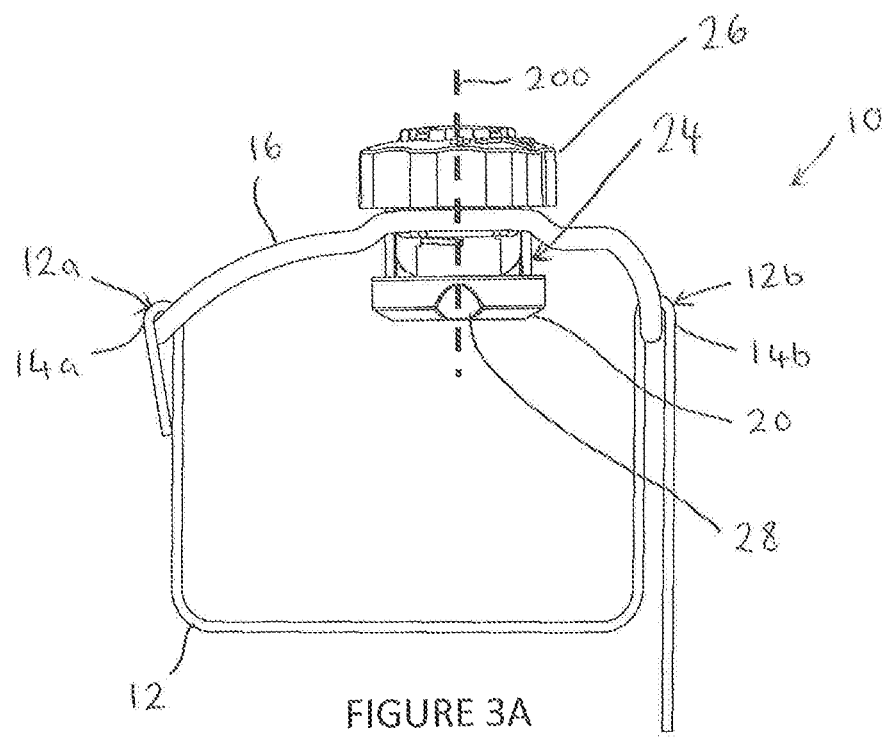
FIG. 3A is a side view of the arterial compression device of FIG. 1.

FIG. 3A shows a side view of the device 10. The pad 20 is arranged so that it is able to move relative to the wrist plate 16 in directions along an axis 200 that is substantially perpendicular to a general plane of the wrist plate 16 (and parallel to the plane 100). In particular, in the embodiment shown in FIG. 3A, the pad 20 is connected to a translation mechanism 24 for translating the pad 20 up and down along the axis 200 to selectively apply pressure to the radial artery. The translation mechanism 24 includes a knob 26 that is rotatable about axis 200 to cause translation of the pad 20 along axis 200. The translation mechanism 24 may comprise any suitable mechanism for translating the pad 20 along axis 200. In certain embodiments (such as the one depicted in the Figures), the translation mechanism 24 may be actuated by rotation of a knob. In certain embodiments, the translation mechanism 24 may comprise cooperating screw threads such that rotation of the screw threads relative to one another results in axial movement of a part of the translation mechanism 24 relative to another part of the translation mechanism 24 along axis 200, where such axial movement is utilized to cause translation of the pad 20 along axis 200. In alternative embodiments, the translation mechanism 24 may comprise a cam arrangement where rotation of one part of the cam arrangement about axis 200 results in axial movement of another part of the cam arrangement along axis 200, where such axial movement is utilized to cause translation of the pad 20 along the axis 200. Such a knob 26 advantageously permits fine adjustments to the compression applied to the radial artery. The knob 26 is manufactured from a transparent or translucent material so that the user may advantageously visually align the device 10 in the correct position on the patient's wrist.

Figure 3B:
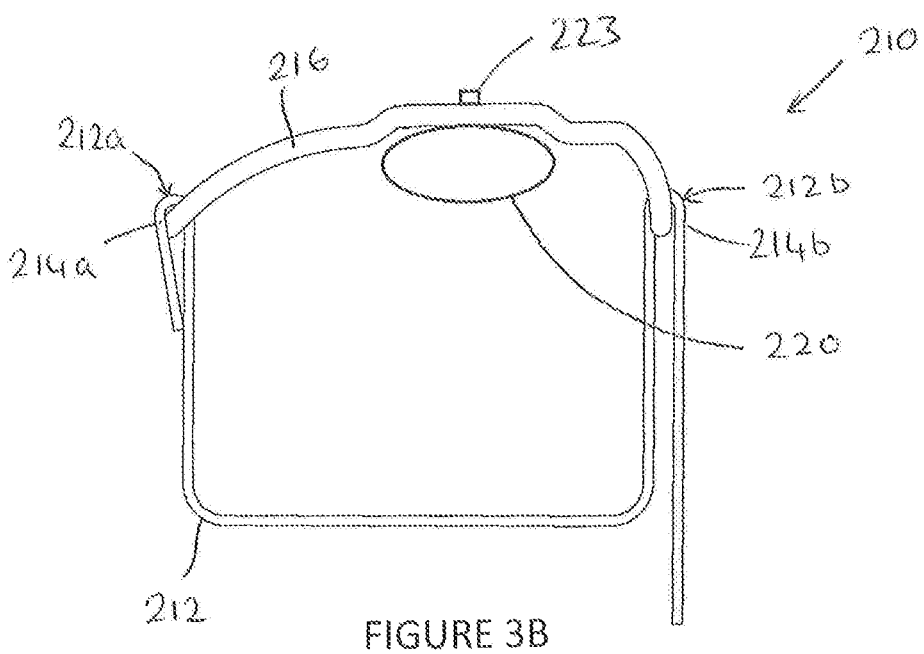
FIG. 3B is a side view of an arterial compression device according to an alternative embodiment of the present disclosure.

In an alternative embodiment that is illustrated in FIG. 3B, a device 210 that is otherwise identical to the device 10 described above (where the same reference numerals are used for equivalent features but with a leading '2') has a compression portion in the form of an inflatable bladder 220. The inflatable bladder 220 has an opening 223 that permits the bladder 220 to be inflated with a fluid and optionally subsequently deflated. In certain embodiments the opening 223 may be an inlet, and a separate dedicated outlet (not shown) may also be provided, where the inlet permits introduction of a fluid for inflating the bladder 220 and the outlet permits fluid to be evacuated from the bladder 220. The fluid may be a gas (e.g. air) or a liquid. The opening 223 (and/or outlet) may include a valve to permit fluid flow in a single direction. In alternative embodiments, closure means such as a cap or stopper may be provided for selectively sealing fluid in the bladder 220.

The bladder 220 may be selectively inflated for selectively applying pressure to the radial artery of the subject when the device 210 is secured around the wrist of the subject. In accordance with the present disclosure, and as described above with reference to device 10, the device 210 includes an aperture (not visible in FIG. 3B) for permitting access to the ulnar artery when the device 210 is secured around the wrist of the subject.

Devices in accordance with the present disclosure may be used to selectively apply pressure to the radial artery and concurrently permit manual pressure to be applied to the ulnar artery of the same wrist of the patient. Devices in accordance with the present disclosure may thus be used to assess blood flow through the radial and/or ulnar arteries according to any suitable method (e.g. the Barbeau test or the Allen test). Devices in accordance with the present disclosure may thus be used to assess whether a patient has achieved patent hemostasis following removal of a sheath/catheter from their radial artery.

In accordance with an aspect of the present disclosure, there is provided a method of assessing radial artery patency in a subject comprising:
  (i) providing an arterial compression device according to any of the embodiments described herein;
  (ii) securably fastening the arterial compression device around the wrist of the subject;
  (iii) moving the compression portion to apply pressure to the radial artery of the subject;
  (iv) manually occluding the ulnar artery of the wrist by applying pressure to the wrist through the aperture;
  (v) making a first determination of a pulse of the subject in a finger of a hand connected to the wrist;
  (vi) moving the compression portion to reduce the pressure applied to the radial artery;
  (vii) making a second determination of the pulse of the subject in the finger of the hand connected to the wrist;
  (viii) comparing the first determination with the second determination; and
  (ix) determining whether radial artery patency has been achieved based on the comparison.

If pressure applied to the radial artery in step (iii) results in occlusion of the radial artery, additional occlusion of the ulnar artery in step (iv) should result in substantially no pulse in the finger of the hand connected to the wrist (as determined at step (v)). By reducing the pressure applied to the radial artery in step (vi), a pulse should return to the finger, provided that the radial artery is not otherwise occluded. Therefore, if the comparison of step (viii) shows that the pulse has increased from the first determination (of step (v)) to the second determination (of step (vii)) then this is indicative of radial artery flow and hence radial artery patency (which is determined at step (ix)). If there is also no blood loss at the puncture site, then this is indicative of patent hemostasis.

The determination of the pulse at steps (v) and (vii) may be performed according to any suitable known method. In certain embodiments, a pulse oximeter is used to measure the pulse of the subject. In particular, a pulse oximeter may be placed on a finger (e.g. the index finger) of the hand connected to the wrist that the device 10 is disposed on to make the first determination (of step (v)) and/or the second determination (of step (vii)).

Returning to FIG. 1, it can be seen that the device 10 includes a groove 28 formed in the pad 20. The groove 28 may assist aligned removal of a cannula from a puncture site under the pad. For example, in applications where the device 10 is being used to achieve and/or check for patent hemostasis following transradial catheterization, the device 10 will be placed around the wrist of a subject whilst a cannula is extending out from the radial artery through a puncture site. The pad 20 may be moved towards the puncture site so that the cannula protrudes from the radial artery and is received in the groove 28. The cannula may then be withdrawn from the radial artery whilst pressure is applied to the radial artery by the pad 20. The groove 28 may facilitate removal of the cannula along a direction that is substantially parallel to the longitudinal axis of the cannula to as to reduce trauma around the puncture site. Whilst the embodiment shown in FIG. 1 only shows one groove 28, it is desired that two grooves 28 are formed in the pad 20 with the second groove (not shown) being positioned at an opposite end of the pad 20 to the groove 28 shown in FIG. 1. This may advantageously allow the device 10 to be worn on either the left or right wrist of a patient. The cannula may only be received in one of the grooves 28 depending on whether the device 10 is worn on the left or right wrist of the patient.

In certain embodiments, some or all of the components of the device may be transparent or translucent. For example, the wrist plate and/or compression portion may be transparent and/or translucent. Such embodiments permit a visual inspection of the puncture site during use of the device (e.g. for checking if the puncture site is bleeding).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

The readers attention is directed to all papers and documents which are filed concurrently with or previous to this specification in connection with this application and which are open to public inspection with this specification, and the contents of all such papers and documents are incorporated herein by reference.

The invention claimed is:

1. An arterial compression device comprising:
a band for securely fastening the arterial compression device around, a wrist of a subject;
a wrist plate having a first end and a second end, wherein the band is connected to the wrist plate at the first end and the second end;
a compression portion that is moveable toward or away from the wrist plate so as to selectively apply pressure to the radial artery of the subject, the compression portion being connected to the wrist plate;
an aperture permitting access to the ulnar artery of the subject when the arterial compression device is securably fastened around the wrist of the subject, wherein the aperture is formed by both the wrist plate and the band, and is bound on one side by an edge of the wrist plate and on an another side by an edge of the band, the aperture sized to provide substantially unobstructed access for at least one thumb tip to pass therethrough so as to temporarily occlude the ulnar artery.

2. The arterial compression device of claim 1, wherein the compression portion includes a pad for contacting the wrist of the subject to apply pressure to the radial artery of the subject.

3. The arterial compression device of claim 2, wherein the pad comprises silicone.

4. The arterial compression device of claim 2, further comprising a rotatable knob that is rotatably coupled to the pad such that rotation of the knob about an axis causes movement of the pad along the axis.

5. The arterial compression device of claim 2, wherein the pad includes at least one groove for accommodating a cannula inserted into a puncture site of the subject beneath the pad when the pad is in contact with the wrist of the subject.

6. The arterial compression device of claim 1, wherein, the compression portion comprises an inflatable balloon for applying pressure to the radial artery of the subject.

7. The arterial compression device of claim 1, wherein the aperture has a generally quadrilateral shape that is bound on at least three sides by the wrist plate.

8. The arterial compression device of claim 1, wherein the wrist plate is transparent or translucent.

9. The arterial compression device of claim 1, wherein the aperture has a width of at least 2 cm and/or has a length of at least 2 cm.

10. The arterial compression device of claim 1, wherein the aperture encompasses an area of at least 2×2 cm2.

11. The arterial compression device of claim 1, wherein the compression portion is transparent or translucent.

12. The arterial compression device of claim 1, further comprising a rotatable knob that is coupled to the compression portion such that rotation of the knob moves the compression portion substantially perpendicular with respect to the wrist plate so as to selectively apply pressure to the radial artery of the subject.

13. The arterial compression device of claim 1 wherein the aperture is formed through both the wrist plate, and the band.

14. An arterial compression device comprising:
a band for securely fastening the arterial compression device around a wrist of a subject;
a wrist plate having a first end and a second end, wherein the band is connected to the wrist plate at the first end and the second end, wherein an aperture is formed by both the wrist plate and the band, and is bound on one side by an edge of the wrist plate and on an another side by an edge of the band, the aperture sized to provide substantially unobstructed access for at least one thumb tip to pass therethrough so as to temporarily occlude the ulnar artery;
a compression portion that is moveable with respect to the wrist plate so as to selectively apply pressure to the radial artery of the subject;
wherein the compression portion includes a pad for contacting the wrist of the subject to apply pressure to the radial artery of the subject; and the pad includes a groove for accommodating a cannula inserted into a puncture site of the subject beneath the pad when the pad is in contact with the wrist of the subject.

15. The arterial compression device of claim 14 wherein the aperture is formed through both the wrist plate and the band.

* * * * *